United States Patent
Durvasula et al.

(10) Patent No.: US 10,194,933 B2
(45) Date of Patent: Feb. 5, 2019

(54) CLAMP ULTRASOUND PROBE FOR LUNG SURGERY

(71) Applicant: Covidien LP, Mansfield, MA (US)

(72) Inventors: Ravi Durvasula, New Haven, CT (US); Wei Tan, Shanghai (CN); Haiying Liu, Winchester, MA (US); Jiqi Cheng, North Haven, CT (US)

(73) Assignee: Covidien LP, Mansfield, MA (US)

( * ) Notice: Subject to any disclaimer, the term of this patent is extended or adjusted under 35 U.S.C. 154(b) by 620 days.

(21) Appl. No.: 14/775,224

(22) PCT Filed: Mar. 11, 2014

(86) PCT No.: PCT/US2014/023087
§ 371 (c)(1),
(2) Date: Sep. 11, 2015

(87) PCT Pub. No.: WO2014/164643
PCT Pub. Date: Oct. 9, 2014

(65) Prior Publication Data
US 2016/0030077 A1    Feb. 4, 2016

Related U.S. Application Data

(60) Provisional application No. 61/778,471, filed on Mar. 13, 2013.

(51) Int. Cl.
*A61B 17/32* (2006.01)
*A61B 17/29* (2006.01)
(Continued)

(52) U.S. Cl.
CPC ........ *A61B 17/320092* (2013.01); *A61B 8/12* (2013.01); *A61B 8/4209* (2013.01);
(Continued)

(58) Field of Classification Search
CPC .... A61B 17/320068; A61B 17/320092; A61B 8/12; A61B 8/4209; A61B 8/445
See application file for complete search history.

(56) References Cited

U.S. PATENT DOCUMENTS 6,569,178 B1    5/2003  Miyawaki et al.
7,229,431 B2 *  6/2007  Houser ............... A61F 2/95
                                                     604/103.04
(Continued)

FOREIGN PATENT DOCUMENTS

EP    1974771 A1    10/2008
WO    2012135721 A1  10/2012
(Continued)

OTHER PUBLICATIONS

International Search Report for (PCT/US2014/023087) date of completion is Jul. 16, 2014 (4 pages).
(Continued)

*Primary Examiner* — Anu Ramana

(57) ABSTRACT

An ultrasonic surgical instrument is disclosed, and includes a handle assembly, an elongate tubular member, and an end effector. The elongate tubular member extends from the handle assembly and defines a channel therethrough. The end effector is coupled with a distal end of the elongate tubular member and includes a first jaw member pivotably attached to the tubular member, and a second jaw member longitudinally movable within the channel of the elongate tubular member. One of the first jaw member and the second jaw member includes at least one ultrasonic transducer.

12 Claims, 3 Drawing Sheets

(51) Int. Cl.
*A61B 8/12* (2006.01)
*A61B 8/00* (2006.01)
*A61B 17/295* (2006.01)
*A61B 90/30* (2016.01)
*A61B 17/00* (2006.01)
*A61B 18/00* (2006.01)
*A61B 90/00* (2016.01)

(52) U.S. Cl.
CPC .............. *A61B 8/445* (2013.01); *A61B 17/29* (2013.01); *A61B 17/295* (2013.01); *A61B 17/2909* (2013.01); *A61B 90/30* (2016.02); *A61B 2017/00026* (2013.01); *A61B 2017/00084* (2013.01); *A61B 2017/00106* (2013.01); *A61B 2017/00199* (2013.01); *A61B 2017/2947* (2013.01); *A61B 2018/0063* (2013.01); *A61B 2018/00577* (2013.01); *A61B 2018/00589* (2013.01); *A61B 2018/00595* (2013.01); *A61B 2090/3784* (2016.02)

(56) References Cited

U.S. PATENT DOCUMENTS

| | | | |
|---|---|---|---|
| 7,776,037 B2* | 8/2010 | Odom | A61B 18/1445 606/51 |
| 7,918,848 B2* | 4/2011 | Lau | A61B 17/29 606/29 |
| 8,308,725 B2 | 11/2012 | Bell et al. | |
| 8,444,664 B2 | 5/2013 | Balanev et al. | |
| 2003/0014093 A1 | 1/2003 | Makin | |
| 2010/0063526 A1 | 3/2010 | Beaupre et al. | |
| 2012/0010506 A1* | 1/2012 | Ullrich | A61B 1/00045 600/440 |
| 2012/0116267 A1 | 5/2012 | Kimball et al. | |

FOREIGN PATENT DOCUMENTS

| | | |
|---|---|---|
| WO | WO-2012-135721 | 10/2012 |
| WO | 2013029664 A1 | 3/2013 |

OTHER PUBLICATIONS

International Search Report dated Jul. 17, 2014, issued in PCT/US2014/023087.
Written Opinion of the International Searching Authority, issued in PCT/US2014/023087.
Chinese Office Action dated Feb. 6, 2017, issued in CN Appln. No. 2014800145013.
European Search Report dated Oct. 14, 2016, issued in European Application No. 14779302.
Chinese Office Action dated Nov. 3, 2017, issued in CN Appln. No. 2014800145013.

* cited by examiner

CLAMP ULTRASOUND PROBE FOR LUNG SURGERY

CROSS-REFERENCE TO RELATED APPLICATIONS

This application is a U.S. National Stage Application filed under 35 U.S.C. § 371(a) of International Patent Application No. PCT/US2014/023087, filed Mar. 11, 2014, which claimed benefit of, and priority to, U.S. Provisional Patent Application 61/778,471, filed on Mar. 13, 2013. The entire contents of each of the above applications is hereby incorporated by reference.

BACKGROUND

1. Technical Field

The present disclosure relates to an apparatus for imaging and treating tissue structures with ultrasonic energy, and in particular to an apparatus having a variable configuration to accommodate tissue structures of different shapes and sizes.

2. Discussion of Related Art

Today, many surgical procedures are performed through small openings in the skin, as compared to the larger openings typically required in traditional procedures, in an effort to reduce both trauma to the patient and recovery time. Generally, such procedures are referred to as endoscopic, unless performed on the patient's abdomen, in which case the procedure is referred to as laparoscopic. Throughout the present disclosure, the term "minimally invasive" should be understood to encompass endoscopic, laparoscopic and robotic procedures.

During the course of minimally invasive procedures, the nature of the relatively small opening through which surgical instruments are manipulated, and/or the presence of sub-surface tissue structures, may obscure a direct line-of-sight to the target surgical site. Even dedicated visualization tools, e.g., cameras, endoscopes, and the like, may be limited by the geometry of a minimally invasive surgical site. Accordingly, it would be desirable to provide a method of sub-surface visualization that is not limited by the geometry of the minimally invasive surgical site. It would further be desirable to treat sub-surface tissue structures with ultrasonic energy.

One such technique involves the use of ultrasound to provide clinicians with the ability to image, diagnose and treat sub-surface tissue structures. Ultrasound imaging relies on different acoustic impedances of adjacent tissue structures to provide the contrast used for imaging and identifying separate tissue structures. Ultrasound imaging possesses several advantages that are attractive for real-time application in surgical procedures, e.g., minimal associated non-ionizing radiation and relatively small and inexpensive imaging hardware. Further, imaging data obtained from many ultrasound imaging procedures is collected instantly and at localized points within a patient, as opposed to collected from a large imaging vessel in which a patient is positioned, allowing real-time assessment to tissue morphology and real-time treatment.

The application of ultrasound energy to tissue may be also be used to increase the amount of heat within tissue e.g., to ablate, melt, seal, char, necrose, or cauterize tissue. In this manner, the use of ultrasound energy to treat tissue may obviate the need for solid instruments to alter or physically separate tissue.

Some surgical apparatuses utilize approximating jaws to capture tissue therebetween, positioning the tissue for the application of ultrasonic energy thereto. However, challenges are presented in capturing and treating tissue having irregular or complex geometries. Accordingly, it would be desirable to provide a surgical apparatus having approximating jaws that are reconfigurable to capture tissue having irregular or complex geometries. Further, a desired site for tissue treatment or imaging, e.g., a cancerous or diseased node, may be located deep within a tissue mass. Accordingly, it would be further desirable to provide a surgical apparatus configured to image or treat a tissue mass from more than one side of the tissue mass, such that ultrasonic energy may be applied to the node from different directions.

SUMMARY

The present disclosure, in accordance with various embodiments thereof, is directed to an ultrasound surgical apparatus. According to one aspect of the present disclosure, an ultrasonic surgical instrument is disclosed, and includes a handle assembly, an elongate tubular member, and an end effector. The elongate tubular member extends from the handle assembly and defines a channel therethrough. The end effector is coupled with a distal end of the elongate tubular member and includes a first jaw member pivotably attached to the tubular member, and a second jaw member longitudinally movable within the channel of the elongate tubular member. One of the first jaw member and the second jaw member includes at least one ultrasonic transducer.

According to another aspect of the present disclosure, a drive member is disposed through the elongate tubular member, the drive member operatively interconnecting the handle assembly and the end effector. The handle assembly may be operatively coupled with the end effector such that actuation of the handle assembly causes the first jaw member to pivot relative to the second jaw member. The handle assembly may be operatively coupled with the end effector such that actuation of the handle assembly causes the second jaw member to translate longitudinally within the channel of the elongate tubular member.

According to another aspect of the present disclosure, the first jaw member is configured to pivot toward the second jaw member to compress tissue therebetween. According to a further aspect of the present disclosure, the at least one ultrasonic transducer is configured to receive ultrasonic energy. In yet another aspect of the present disclosure, the at least one ultrasonic transducer is configured to transmit ultrasonic energy. In another aspect of the present disclosure, each of the first jaw member and the second jaw member includes at least one ultrasonic transducer. The respective at least one ultrasonic transducer of the first jaw member and the second jaw member are together configured to receive ultrasonic energy reflected from opposite sides of tissue disposed therebetween.

According to another aspect of the present disclosure, a method of using an ultrasonic surgical instrument is disclosed, and includes providing a handle assembly, providing an elongate tubular member extending from the handle assembly and defining a channel therethrough, providing an end effector coupled with a distal end of the elongate tubular member and operatively coupled with the handle assembly. The end effector is provided including a first jaw member pivotably arranged with respect to the elongate tubular member, and a second jaw member translatable with respect to the channel. The method also includes providing an ultrasonic transducer on one of the first jaw member and the second jaw member. The method also includes actuating the handle assembly such that the first jaw member pivots toward the second jaw member to capture tissue therebetween. The method further includes activating the ultrasonic transducer such that ultrasonic energy is emitted therefrom.

According to a further aspect of the present disclosure, the method includes actuating the handle assembly such that the second jaw member moves within the channel of the elongate tubular member. According to another aspect of the present disclosure, the tissue may be heated to a predetermined temperature using the ultrasound transducer. The transducer may be an array transducer.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION OF THE DRAWINGS

Figure 1:
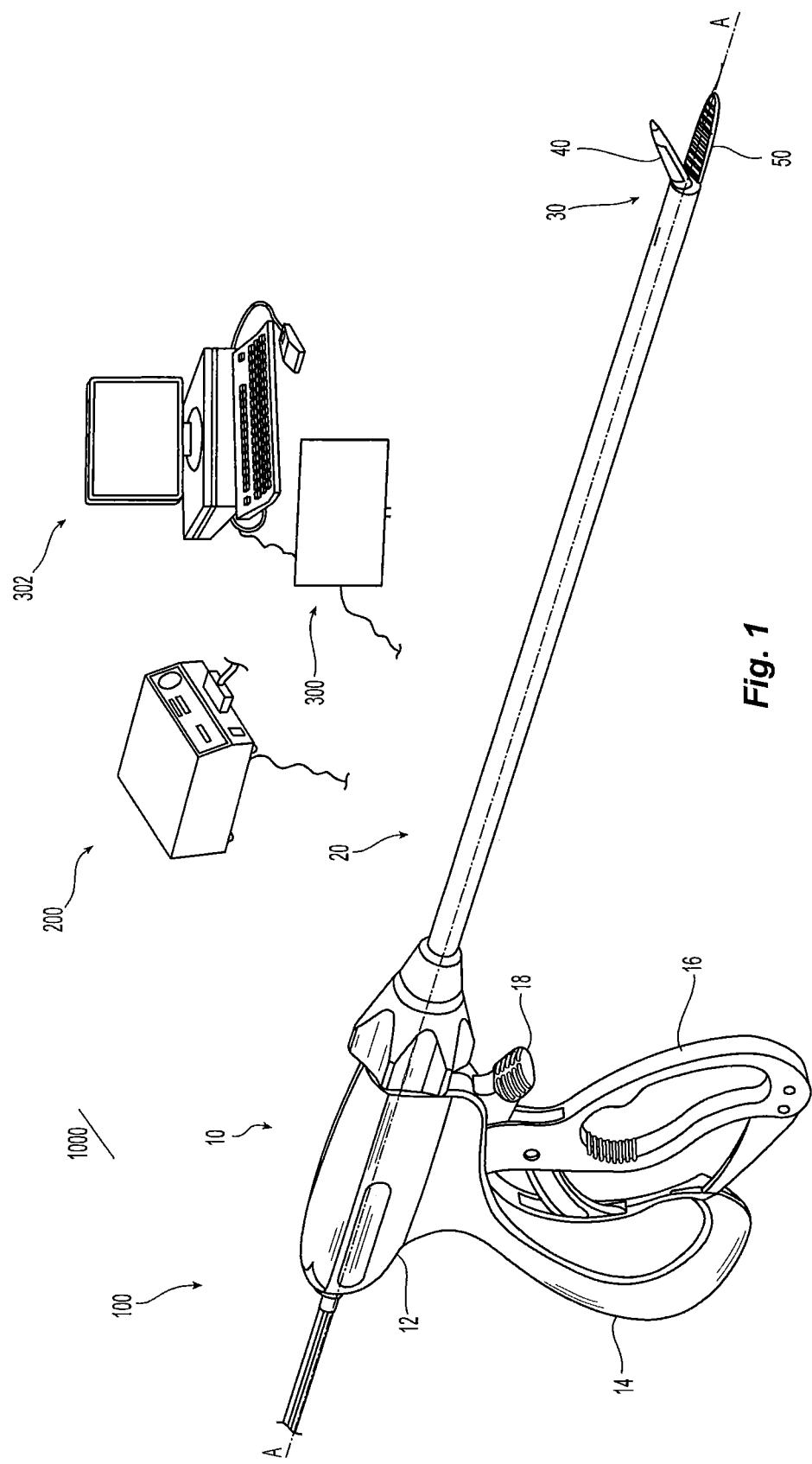
FIG. 1 is a perspective view of an ultrasound surgical system including an ultrasound surgical apparatus according to the present disclosure.

Embodiments of the presently disclosed surgical ultrasound system and surgical imaging apparatus will now be described in detail with reference to the figures, in which like reference numerals identify corresponding elements throughout the several views.

As would be appreciated by one skilled in the art, the terms "ultrasound" and "ultrasonic", as used herein, are intended to be interchangeable.

Referring initially to FIG. 1, an ultrasound system 1000 includes an ultrasonic surgical apparatus 100. Ultrasonic surgical apparatus 100, as shown may also be coupled with an ultrasonic generator 200, a processor 300, and a display 302. Each of the ultrasonic generator 200, processor 300, and display 302 may be electrically coupled with the ultrasound surgical apparatus 100, as will be described further below.

Surgical apparatus 100, as shown, includes a handle assembly 10, an elongate shaft member 20 extending therefrom and defining a longitudinal axis "A", and an end effector 30 coupled to a distal portion of the shaft member 20.

Handle assembly 10 generally includes a housing 12, a stationary handle 14, and a movable handle 16 configured to approximate toward the stationary handle 14 to actuate the ultrasonic surgical apparatus 100 and cause movement of the end effector 30. A trigger 18 may also cause movement of the end effector 30, as will be described further below. A more detailed description of the features and function of handle assembly 10 and subsequent actuation thereof are disclosed in U.S. Pat. No. 5,865,361 to Milliman et al., the entire contents of which are incorporated herein by reference.

Figure 2A:
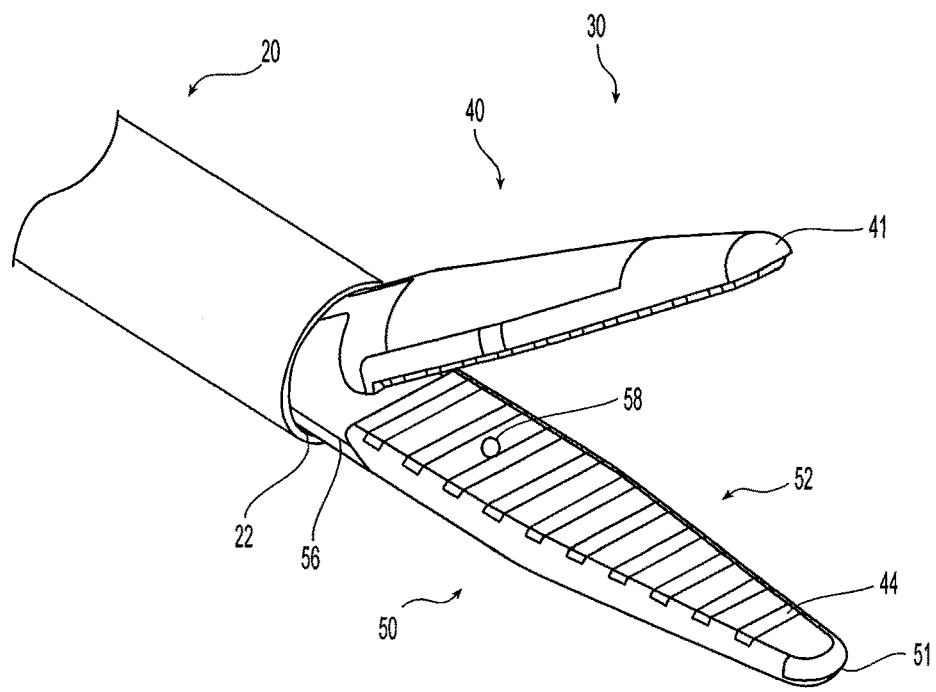
FIG. 2A is a perspective view of the end effector portion of the ultrasound surgical apparatus.

Shaft assembly 20, as shown, is a substantially straight, tubular member defining a channel 22 therethrough (FIG. 2A). Channel 22 is configured to receive a portion of the end effector 30, as will be described further below. Shaft assembly 20 may be coupled to the handle assembly 10 in any suitable manner, e.g., adhesion or welding, snap fit, interference fit, or press fit.

End effector 30, as shown, includes a first jaw member 40 and a second jaw member 50. First jaw member 40 is pivotably attached to a distal portion of the shaft member 20. Accordingly, first jaw member 40 is configured to approximate, i.e., pivot radially toward, second jaw member 50 to capture tissue therebetween, as will be described further below. Additionally, second jaw member 50 is configured to axially translate with respect to the shaft member 20 to reconfigure the relative positioning of first jaw member 40 and second jaw 50, as will be described further below. First jaw member 40 and second jaw member 50 are configured to move independently of each other. While jaw members 40 and 50 are depicted as having jaws that converge distal, jaws 40 and 50 may be rectangular or other shapes, such as curved jaws.

Figure 2B:
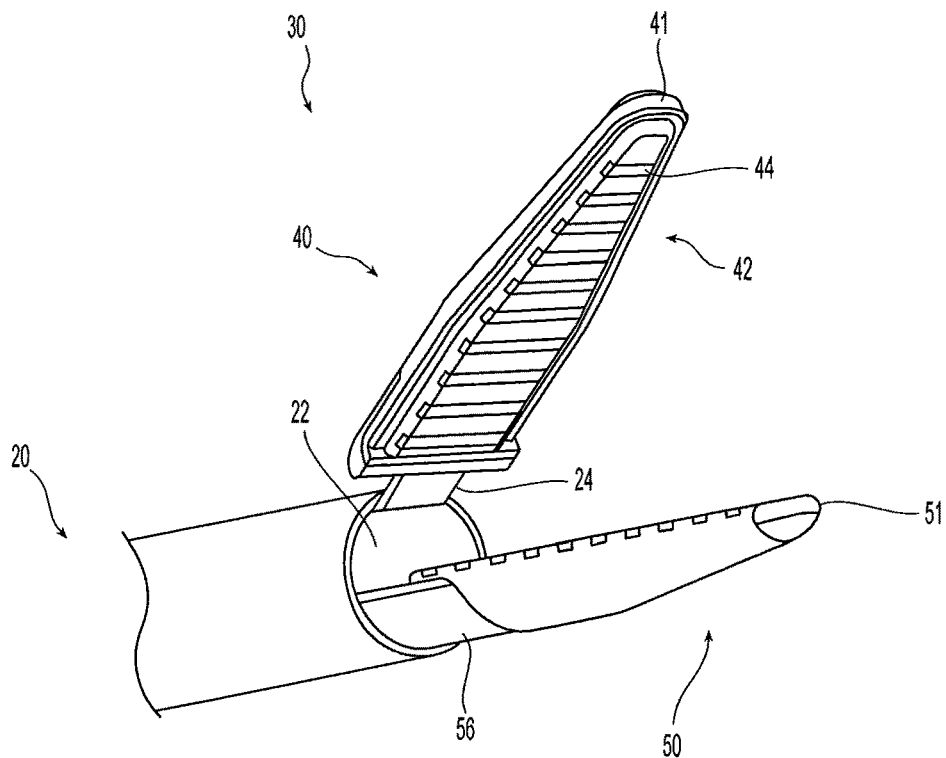
FIG. 2B is another perspective view of the end effector portion of the ultrasound surgical apparatus.

Turning now to FIGS. 2A and 2B, the end effector 30 is shown in detail. First jaw member 40 is pivotably connected to the shaft member 20 via a hinge 24. Hinge 24 may include a pivot point on one or more of the shaft member 20 and the first jaw member 40, and is configured to approximate toward the second jaw member 50 upon actuation of the handle assembly 10 (FIG. 1) as described above. First jaw member 40 may be actuated by the handle assembly 10, and is acted upon by the action of, e.g., a drive member, drive cable, or dynamic clamping member. In embodiments, hinge 24 may be configured as a leaf spring to maintain first jaw member 40 in a resting, unapproximated position.

First jaw member 40, as shown, has tapered profile along the longitudinal axis A (FIG. 1) to define a distal surface 41 that is configured to make an initial contact with a tissue surface, e.g., to push, move, or dilate tissue. First jaw member 40 also defines a tissue contacting surface 42. Tissue contacting surface 42, as shown, may have a substantially flat profile, and may including a plurality of ultrasound transducers 44 thereon. Ultrasound transducers 44 may be arranged in longitudinally spaced rows, as shown, or may have any other desirable arrangement on tissue contacting surface 42 of first jaw member 40.

Ultrasound transducers 44 may be any type of transducer or sensor that is configured to detect the presence and/or properties, e.g., amplitude, of ultrasonic energy. Accordingly, ultrasound transducers 44 are configured to convert energy reflected off tissue structures having different acoustic impedances into distinct electrical signals, as will be described further below. In embodiments, ultrasound transducers 44 may be configured to generate and/or transmit ultrasonic energy as well as to receive energy.

Figure 3:
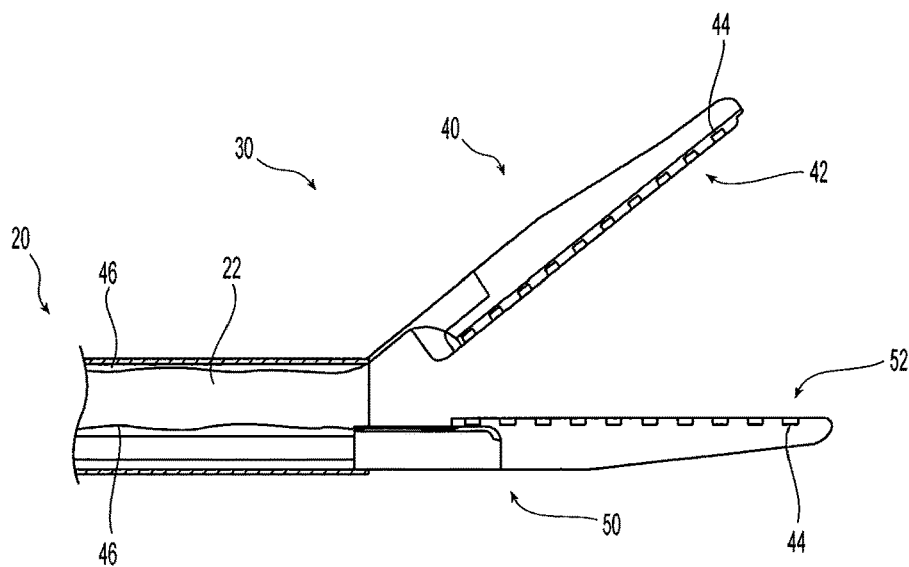
FIG. 3 is a side view, shown partially in cutaway of the end effector portion of the ultrasound surgical apparatus.

Accordingly, ultrasound transducers 44 may be electrically coupled to a power source through electrical wires 46 (FIG. 3). Electrical wires may be any type of cable or conduit suitable for transmitting electrical energy between ultrasound transducers 44 and a source of electrical energy, e.g., a battery, generator, or local power grid (not shown). Electrical wires 46 may also electrically couple ultrasound transducers 44 with ultrasound generator 200, processor 300, and/or display 302 (FIG. 1).

Second jaw member 50, as shown, is aligned radially within the interior wall of the shaft member 20 that defines channel 22. Accordingly, second jaw member 50 is disposed such that second jaw member 50 is aligned for passage into the channel 22. Second jaw member 50 is supported on a drive member 56 that extends proximally through the channel 22 of shaft member 20, and is operably coupled with trigger 18 of the handle assembly 10 (FIG. 1). Drive member 56 is operably coupled with the trigger 18 of the handle assembly 10 such that actuation of the trigger 18 causes withdrawal or extension of the drive member 56, and the second jaw member 50 attached thereto, relative to the shaft member 20. In some embodiments, the drive member 56 may be spring loaded with respect to trigger 18 such that second jaw member 50 is biased toward a resting, extended position. Because the second jaw member 50 is aligned with the channel 22 of the shaft member 20, second jaw member 50 may be positioned to translate partially or entirely within the channel 22 of the shaft member 20. Drive member 56 and second jaw member 50 may be attached in any suitably secured manner, e.g., adhered, welded, brazed, press fit, interference fit, snap fit, etc.

Second jaw member 50 has a similar configuration to first jaw member 40 described above. In particular, second jaw member 50 has a substantially tapered profile along the longitudinal axis A to define a distal surface 51 that is configured to make an initial contact with tissue, e.g., to press, move, or dilate tissue. Second jaw member 50 also defines a tissue contacting surface 52. Tissue contacting surface 52 may have a substantially flat profile, as shown, and includes a plurality of ultrasound transducers 44 thereon. Ultrasound transducers 44 may be arranged in any suitable manner, e.g., longitudinally spaced rows, as described above with respect to first jaw member 40. Accordingly, the ultrasound transducers 44 of the second jaw member 50 may be electrically coupled with ultrasound generator 200 (FIG. 1) via wires 46 to transmit ultrasonic energy therethrough.

It will be understood that the components of ultrasound surgical apparatus 100 may have any desirable configuration or arrangement. In some embodiments, ultrasound transducers 44 may be present on only one of first and second jaw members 40, 50. Additionally, the components of ultrasound surgical apparatus 100 may be formed of any suitable materials for their respective purposes, e.g., biocompatible polymers, metals, or composites. It will further be understood that while ultrasound surgical apparatus 100 has been described with respect to use in minimally invasive procedures, ultrasound surgical apparatus 100 is suitable for use in traditional open-type surgical procedures.

Figure 4:
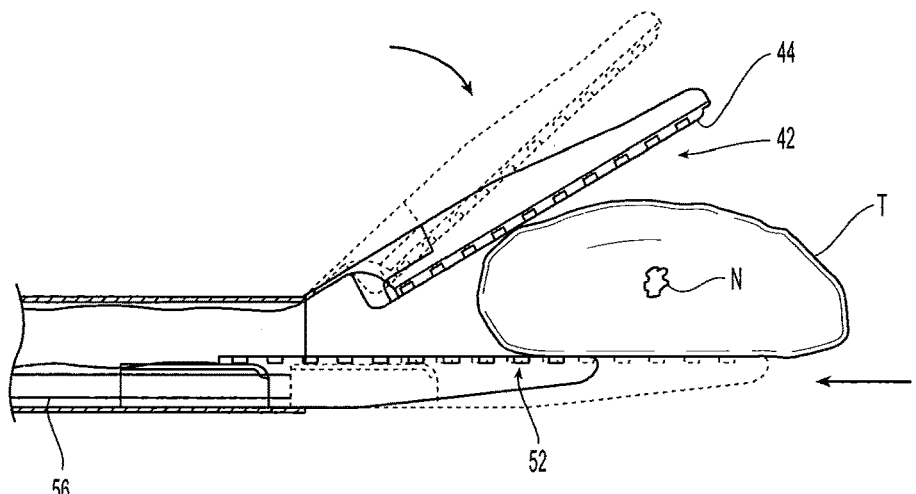
FIG. 4 is a side view, shown partially in cutaway, of the end effector portion of the ultrasound surgical apparatus treating tissue.
Figure 5:
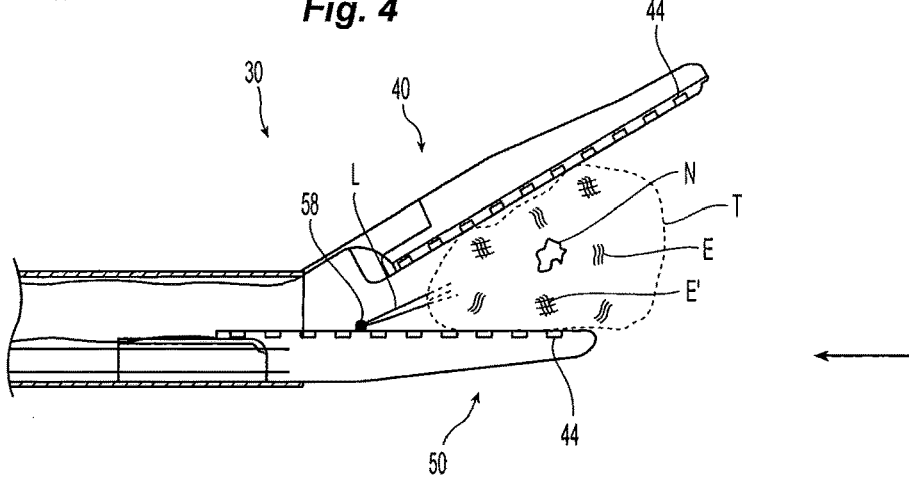
FIG. 5 is another side view, shown partially in cutaway, of the end effector portion portion of the ultrasound surgical apparatus treating tissue.

Turning to FIGS. 3, 4, and 5, the operation of surgical apparatus 100 will be described in detail.

As described above, the first jaw member 40 is configured to pivot at hinge 24 to move from a first, open position, to a second, approximated position. Accordingly, end effector 30 is configured to close about and capture, e.g., a section of tissue "T". First jaw member 40 may be forced to exert a compressive force on tissue T against second jaw member 50 such that tissue T is compressed therebetween. In embodiments, first jaw member 40 may be configured to exert a variable or user-defined compressive force on tissue T.

Tissue T may be any portion of tissue, and may include a target region for imaging or treatment, e.g., a node "N". Node N may be, e.g., a diseased or cancerous portion of tissue T. As shown, node N may be disposed in an interior portion of the tissue T. Additionally, tissue T may have an irregular shape such that the approximation of first jaw member 40 toward second jaw member 50 may capture a portion of the tissue T, while another portion of tissue T including node N is spaced away from jaw members 40, 50. As node N is a target region within tissue T, it is desirable to bring node N in close proximity with tissue contacting surfaces 42, 52, as well as to maximize the amount of surface contact between tissue contacting surfaces 42, 52 and tissue T. Accordingly, it may be desirable to reconfigure the relative placement of jaw members 40, 50. Thus, jaw member 50 may be withdrawn proximally into the channel 22 of shaft member 20, e.g., to draw the portion of tissue T containing node N proximally therewith and present a larger surface area for the tissue contacting surface 42 of the first jaw member 40 to contact tissue T. Thereafter, the second jaw member 50 may be again moved distally to maximize the amount of contact between the second tissue contacting surface 52 and the tissue T (not shown).

Once tissue T is appropriately disposed between the jaw members 40, 50, ultrasonic transducers 44 are activated and ultrasonic energy E is applied to the tissue T. Ultrasound transducers 44 may be configured to generate and transmit ultrasonic energy "E", e.g., an ultrasonic wave, to tissue T. Ultrasonic energy may be transmitted to ultrasound transducers 44, e.g., via ultrasound generator 200 (FIG. 1). In embodiments, ultrasound generator 200 is configured to transmit ultrasonic energy independently of or in conjunction with ultrasound transducers 44. Additionally, light source 58 may be activated to illuminate portions of tissue T with light "L".

As ultrasonic energy E is transmitted through tissue T, reflected energy E' is reflected off tissue structures, e.g., tissue surface T. Because ultrasound transducers 44 are located on either side of the tissue T, i.e., ultrasonic transducers 44 are disposed on both the first and second jaw members 40, 50, ultrasonic energy may be applied about either side of a target region of tissue, i.e., node N. Accordingly, a node N that is disposed deep within tissue T such that ultrasound imaging procedures may be obscured by e.g., particularly dense regions of tissue T, can be completed more effectively via the application of ultrasonic energy E to either side of tissue T containing node N. Additionally, the ultrasonic transducers 44 disposed on one of the first and second jaw members 40, 50 may be configured to transmit ultrasonic energy E to the ultrasonic transducers 44 disposed on the other of the first and second jaw members 40, 50, which may be configured to receive reflected energy E' such that ultrasonic energy E passes from one side of the tissue T to another. In this manner, additional properties of tissue T, e.g., thickness or the rate of fluids flowing therethrough, may be measured.

Ultrasound transducers 44, as described above, are configured to receive ultrasound energy E and produce an electrical signal based on the reflected energy E' received. Accordingly, as the reflected ultrasonic energy E' received from different portions of the tissue T has different properties due to the acoustic impedance of different portions of tissue T, ultrasonic transducers 44 produce different electrical signals in response to the reflected ultrasonic energy E' received from those portions of tissue T.

Additionally or alternatively, ultrasonic energy E applied to tissue T may be used to provide heat tissue T, e.g., to ablate, melt, seal, char, or necrose tissue. Accordingly, ultrasonic energy may be applied through ultrasonic transducers 44 such that tissue T, or portions thereof, are raised to a predetermined temperature.

With additional reference to FIG. 1, and as described above, ultrasound surgical apparatus 100 may be electrically coupled with a processor 300, which is configured to interpret the electrical signals received from ultrasonic transducers 44. Accordingly, processor 300 may include a monitor 302 for displaying stored or real-time data, e.g., 2D- or 3D-visual or graphical representations of data collected by the ultrasound transducers 44. In this manner, processor 300 provides an interface, externally of a patient, that enables an operator to visualize sub-surface tissue structures.

Processor 300 may be configured to produce signals in response to the data provided by the ultrasound transducers 44. In some embodiments, the processor 300 may detect a changed condition at the minimally invasive surgical site, e.g., a shift in the positioning of the tissue node N in relation to the ultrasound surgical apparatus 100, or a growth or spreading of node N or another diseased portion of tissue. Such indications may be provided on the monitor 302. Additionally, processor 300 may incorporate a memory storage module, e.g., an onboard or removable memory storage device, EEPROM, or the like, for storing data received from the ultrasonic transducers 44, or for comparison with predetermined values or for providing feedback.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims.

The invention claimed is:

1. A surgical instrument, comprising:
    a handle assembly;
    an elongate tubular member extending from the handle assembly and defining a channel therethrough; and
    an end effector coupled with a distal end of the elongate tubular member and including:
        a first jaw member pivotably attached to the elongate tubular member; and
        a second jaw member longitudinally movable within the channel of the elongate tubular member;
    wherein one of the first jaw member or the second jaw member includes at least one ultrasound transducer configured to provide visualization of tissue adjacent the one of the first jaw member or the second jaw member.

2. The surgical instrument of claim 1, further comprising a drive member disposed through the elongate tubular member, the drive member operatively interconnecting the handle assembly and the end effector.

3. The surgical instrument of claim 2, wherein the handle assembly is operatively coupled with the end effector such that actuation of the handle assembly causes the first jaw member to pivot relative to the second jaw member.

4. The surgical instrument of claim 2, wherein the handle assembly is operatively coupled with the end effector such that actuation of the handle assembly causes the second jaw member to translate longitudinally within the channel of the elongate tubular member.

5. The surgical instrument of claim 1, wherein the first jaw member is movable independently of the second jaw member.

6. The surgical instrument of claim 1, wherein the first jaw member is configured to pivot toward the second jaw member to compress tissue therebetween.

7. The surgical instrument of claim 1, wherein the at least one ultrasound transducer is configured to receive ultrasonic energy.

8. The surgical instrument of claim 1, wherein the at least one ultrasound transducer is configured to transmit ultrasonic energy.

9. The surgical instrument of claim 1, wherein each of the first jaw member and the second jaw member includes at least one ultrasound transducer.

10. The surgical instrument of claim 9, wherein the respective at least one ultrasound transducer of the first jaw member and the second jaw member are together configured to receive ultrasonic energy reflected from opposite sides of tissue disposed therebetween.

11. The surgical instrument of claim 1, wherein one of the first jaw member and the second jaw member includes a light source.

12. The surgical instrument of claim 11, wherein the light source is a laser light source.

* * * * *